United States Patent [19]

Pellicciari et al.

[11] Patent Number: 5,096,898

[45] Date of Patent: Mar. 17, 1992

[54] BILE ACID UNSATURATED DERIVATIVES AND PHARMACEUTICAL COMPOSITIONS CONTAINING THEM

[75] Inventors: Roberto Pellicciari; Aldo Roda, both of Milan, Italy

[73] Assignee: Giuliani S.p.A., Milan, Italy

[21] Appl. No.: 650,751

[22] Filed: Feb. 5, 1991

[30] Foreign Application Priority Data

Feb. 27, 1990 [IT]  Italy ................. 19494 A/90

[51] Int. Cl.$^5$ .................. A61K 31/56; C07J 9/00
[52] U.S. Cl. ................. 514/182; 552/542
[58] Field of Search ............. 552/542; 514/182

[56] References Cited

PUBLICATIONS

Journal of Chromatography, 257, (1983), 411–415.
Journal of Lipid Research,, vol. 24, (1983), 924–929.
Journal of Lipid Research, vol. 24, (1983), 1468–1474.
J. Biochem., 96, 1103–1107, (1984).
Journal of Lipid Research, vol. 23, (1982), 947–954.
Journal of Lipid Research, vol. 27, (1986), 1154–1162.
J. Biochem., 101, 1377–1384, (1987).

Primary Examiner—Howard T. Mars
Assistant Examiner—Kimberly J. Kestler
Attorney, Agent, or Firm—Walter H. Schneider

[57] ABSTRACT

Bile acid derivatives of formula I

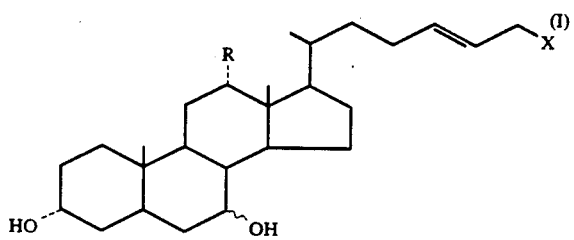

wherein:
R is hydrogen or hydroxy;
X is a carboxy or a $SO_3H$ group, have valuable pharmacologic properties.

8 Claims, No Drawings

BILE ACID UNSATURATED DERIVATIVES AND PHARMACEUTICAL COMPOSITIONS CONTAINING THEM

The present invention relates to bile acid derivatives, to a process for the preparation thereof and to pharmaceutical compositions containing them as the active ingredients.

The compounds of the invention have the following general formula I

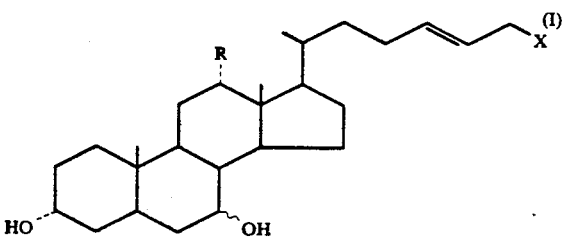

wherein:
R is hydrogen or hydroxy;
X is a carboxy or a $SO_3H$ group.

The present invention also relates to the non toxic salts as well as to the glycine and taurine conjugated forms of the compounds of the invention.

In compounds I, X is preferably a carboxy group.

Bile acids, particularly cholic acid, ursodeoxycholic acid, chenodeoxycholic acid, ursocholic acid, have been used for a long time in human therapy as choleretic, anticholestatic and antilithiasis agents.

Now it has been found that a change in the side chain at the 17-position of the natural molecules by introducing a trans double bond at the 24-position, involves surprising effects on the physico-chemical, biological and biopharmacological characteristics of the compounds of the invention compared with the natural ones.

Particularly, a better metabolic stability, an increase in detergency and lipophilicity, a higher capability to form micells, an increased choleretic effect were evidenced, the secretion of cholesterol and phospholipids being unchanged.

Therefore, compounds I can be used in human therapy for the treatment of all those pathologies on which natural bile acids are known to exert a favourable pharmacological effect. Compounds I can be administered in form of suitable pharmaceutical formulations, which can be prepared according to conventional techniques and excipients, such as those described in "Remington's Pharmaceutical Sciences Handbook", Mack Pub. Co., N.Y., USA.

The envisaged daily dosages will range from 100 mg to 2.5 g depending on the disease to be treated as well as the patient's conditions.

Compounds of formula I are prepared, according to the invention, by reacting compounds of formula II

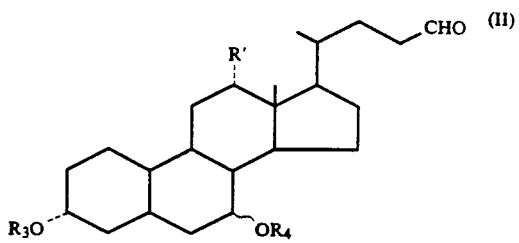

wherein R' is hydrogen or a protected hydroxy group, and $R_3$ and $R_4$ are hydroxy-protecting groups, with a phosphorus ylide of formula III

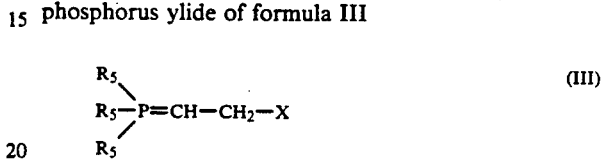

wherein X is as above defined and $R_5$ is an alkyl or phenyl group.

Compounds II can be prepared by reducing the carboxy group of the corresponding natural compounds to aldehyde group. Such a reduction can be carried out by means of any known methods, an indirect route comprising the reduction of the carboxy group to hydroxy group and the subsequent oxidation of the latter to carbonyl group being preferred.

The hydroxy groups in the compounds are of course protected in a conventional way, for instance by formation of ethers, esters, silyl ethers and the like, which are removed after the reaction with the phosphorus ylide.

The reaction of compound II with ylide III is carried out according to known techniques, in anhydrous solvents at low temperature.

Ylide III can also be prepared by known methods, for example by reacting tributylphosphine or triphenylphosphine with compounds of formula

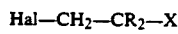

wherein X is as above defined and Hal is a halogen atom, in the presence of strong bases.

The following example further illustrates the invention.

3α,7β-Ditetrahydropyranyloxy-5β-cholan-24-oic acid (2).

Dihydropyrane (20.28 g; 241 mmoles) was dropped in 16 hrs into an ursodeoxycholic acid solution (30.0 g; 76.72 mmoles) and p-toluenesulphonic acid (1.55 g; 8.15 mmoles) in dioxane (160 ml), kept under magnetic stirring at room temperature. At the end of the addition the reaction mixture was concentrated under vacuum, taken up into ethyl ether (100 ml) then washed with water (3×50 ml) and saturated water (1×50 ml). After drying over sodium sulfate and evaporation of the solvents, the residue (45.00 g) was subjected to flash chromatography on $SiO_2$ (φ=5 cm, h=20 cm): eluting with 95/5 chloroform/methanol, 34.4 g of compound (2) were obtained, (80%); $ν_{max}$ (CHCl$_3$) 1710 cm$^{-1}$ (C=O); $^1$H-NMR (CDCl$_3$)δ 0,7 (s, 3H, 18-CH$_3$); 0,9-1,0 (m, 6H, 19-CH$_3$); 3,3-4,05 (m, 6H, 3-CH-, 7-CH-, 2x-OCH$_2$); 4,4-4,7 (m, 2H, 2x-O-CH-O-).

3α,7β-Ditetrahydropyranyloxy-5β-cholan-24-ol (3)

To a solution of compound (2) (9.80 g; 17.48 mmoles) in anhydrous tetrahydrofuran (250 ml), at −70° C. under magnetic stirring and nitrogen atmosphere, N-methylmorpholine (1.76 g; 17.48 mmoles) and isobutyl chloroformate (2.87 g; 21.0 mmoles) were added. The reaction mixture was left to react for 30 min., the separated solid was then removed by filtration and the filtrate was added to a sodium borohydride solution (1.65 g; 43.6 mmoles) in water (10 ml) kept at −10° C. under magnetic stirring at room temperature, in about 30 min., and the resulting mixture was left to react overnight at r.t. Thereafter the reaction mixture was diluted with ethyl acetate (20 ml) and water (80 ml), acidified with 5% hydrochloric acid and extracted with ethyl acetate (3×50 ml). The combined organic phases were washed with saturated water (1×50 ml), dried over sodium sulfate and concentrated under vacuum. A residue (9.40 g) was obtained which was subjected to flash chromatography on $SiO_2$ ($\phi$=5.5 cm, h=20 cm): eluting with 99/1 chloroform/methanol, 6.8 g of compound (3) were obtained, (71%); $^1$H-NMR (CDCl$_3$)δ 0,7 (s, 3H, 18-CH$_3$); 0,9–1,0 (m, 6H, 19-CH$_3$, 21-CH$_3$); 2,15–2,3 (s, 1H, —OH); 3,3–4,1 (m, 8H, 3-CH-, 24-CH$_2$-, 2x-O-CH$_2$-); 4,4–4,75 (m, 2H, 2x-O-CH-O-).

3α, 7β-Ditetrahydropyranyloxy-5β-cholan-24-al (4)

To a solution of oxalyl chloride (8.17 g; 64.35 mmoles) in methylene chloride (140 ml) kept at −70° C. under magnetic stirring and nitrogen atmosphere, di- methylsulfoxide (11.00 g; 141.15 mmoles) diluted in methylene chloride (10 ml) was added in about 10 min. The reaction mixture was left to stand for 10 min., then a solution of compound (3) (29.60 g; 54.15 mmoles) in methylene chloride (20 ml) and dimethylsulfoxide (20 ml) was dropped therein in about 20 min. 15 Min. after, triethylamine (29.73 g; 294.4 mmoles) was added and the resulting mixture was kept under stirring for 10 min. The reaction mixture was warmed to r.t., diluted with water (200 ml), the organic phase was separated and the aqueous one was extracted with methylene chloride (3×50 ml). The combined organic phases were washed with saturated water (1×50 ml), dried over sodium sulfate and concentrated under vacuum. The residue (31.50 g) was subjected to flash chromatography on $SiO_2$ ($\phi$ 5.5 cm, h=25 cm): eluting with 4/6 ethyl ether/petroleum ether, 25.6 g of compound (4) were obtained, (87%); $_{max}$ (CHCl$_3$): 1725 cm$^{-1}$ (C=O); $^1$H-NMR (CDCl$_3$)δ 0,7 (s, 3H, 18-CH$_3$); 0,9–0,95 (m, 6H, 19-CH$_3$, 21-CH$_3$); 3,1–4,1 (m, 6H, 3-CH-, 7-CH- e 2x-OCH$_2$-); 4,35–4,7 (m, 2H, 2x-O-CH-O-); 9,6 (s, 1H, —CHO).

Trans-3α,7β-ditetrahydropyranyloxy-5β-24-cholen-27-oic acid

To a suspension of 2-carboxyethyl(triphenyl)phosphonium chloride (12.30 g; 33.13 mmoles) /previously prepared by reacting 3-chloropropionic acid (7.42 g; 68.38 mmoles) with triphenylphosphine (18.00 g; 68.38 mmoles) in xylene (100 ml) under reflux/ in anhydrous tetrahydrofuran (80 ml) and anhydrous dimethylformamide (20 ml), kept at 0° C. under magnetic stirring and nitrogen atmosphere, a solution of hexamethyldisilazane (12.65 ml; 60.00 mmoles) and n-butyl lithium (31.40 ml; 56.30 mmoles) in anhydrous tetrahydrofuran (40 ml) was added in about 10 min. The reaction mixture was left to react for 15 min. at 0° C., then it was cooled to −70° C. and a solution of compound (4) (9.00 g; 16.52 mmoles) in anhydrous tetrahydrofuran (80 ml) was dropped therein in 40 min. The resulting mixture was left to react at −70° C. for 30 min., at r.t. for 60 min. and under reflux for 4 hrs. The reaction mixture was concentrated under vacuum, the crude product was taken up into ethyl acetate (100 ml), acidified with 2% hydrochloric acid (100 ml), the organic phase was separated and the aqueous one was extracted with ethyl acetate (3×100 ml). The combined organic phases were washed with saturated water (1×100 ml), dried over sodium sulfate and concentrated under vacuum. The residue (20.00 g) was subjected to flash chromatography on $SiO_2$ ($\phi$=4 cm, h=20 cm): eluting first with 6/4 petroleum ether/ethyl ether, then with 98/2 chloroform/methanol, 9.0 g of a solid impure product were obtained. The subsequent purification was carried out suspending the solid in ethyl ether and, after filtration and evaporation of the solvent, 3.00 g of pure compound (5) were obtained (30%); $^1$H-NMR (CDCl$_3$)δ 0,7 (s, 3H, 18-CH$_3$);0,90–1,00 (m, 6H, 19-CH$_3$, 21-CH$_3$); 2,95–3,1 (m, 2H, 26-CH$_2$-); 3,20–4,00 (m, 6H, 3-CH-, 6-CH-, 2x-O-CH$_2$-); 4,3–4,75 (m, 2H, 2x-O-CH-O-); 5,35–6,55 (m, 2H, 24-CH-, 25-CH-); 5,65–6,05 (br, 1H, —COOH).

Trans-3α,7β-dihydroxy-5β-24-cholen-27-oic acid (6)

Concentrated hydrochloric acid (10 ml) was added to a solution of compound (5) (3.00 g; 5.00 mmoles) in tetrahydrofuran (50 ml), kept under magnetic stirring at r.t. The reaction mixture was left to react for 2 hrs., then it was concentrated under vacuum, the residue was taken up into ethyl acetate (100 ml), diluted with water (100 ml), the organic phase was separated and the aqueous one was extracted with ethyl acetate (3×30 ml). The combined organic phases were washed with saturated water (1×50 ml), dried over sodium sulfate and concentrated under vacuum. The residue was flash chromatographed on $SiO_2$ ($\phi$=3.5 cm, h=15 cm): eluting with chloroform containing 2.15% methanol, 1.30 g of compound were obtained (60%);m.p. 156°–161° C.;$\nu_{max}$ (CHCl$_3$) 1710 cm$^{-1}$ (C=O); $^1$H-NMR (CDCl$_3$)δ 0,70 (s, 3H, 18-CH$_3$); 0,9–1,0 (m, 6H, 19-CH$_3$, 21-CH$_3$); 2,96–3,1 (m, 2H, 26-CH$_2$-); 3,5–3,7 (m, 2H, 3-CH-, 7-CH-); 5,4–5,6 (m, 2H, 24-CH-, 25-CH-); 5,8–6,1 (m, 3H, 2x-OH e —COOH); $^{13}$C-NMR [(CO$_3$)-$_2$SO]δ69,38 (C$_3$); 69,64 (C$_7$); 132,36 (C$_{24}$); 133,57 (C$_{25}$); 172,4 (C$_{27}$).

Following the same procedure, but starting from the appropriate bile acids, the following derivatives were prepared:

trans 3α,7α-dihydoxy-5β-24-cholen-27-oic acid
trans 3α,7α,12α-trihydroxy-5β-24-cholen-27-oic acid
trans 3α,7β,12α-trihydroxy-5β-24-cholen-27-oic acid The physico-chemical characteristics of 3,7β-dihydroxy-5β-24-cholen-27-oic acid, hereinafter also defined with the abbreviation TOL-UDCA for sake of shortness, are reported in the following Table 1, in comparison with those of ursodeoxycholic acid (UDCA) and of the glycine and taurine conjugated thereof.

TABLE 1

| | Physico-chemical characteristics | | | |
|---|---|---|---|---|
| | Critical micellar concentration (CMC) | Retention times with $C_{18}$—HPLC(K') | Solubility ($\mu$M) | pKa |
| UDCA | 19 | 3,66 | 9 | 5,06 |
| T-UDCA | 8 | 0,98 | — | 2 |
| G-UDCA | 12 | 1,06 | 3 | 3,90 |
| TOL-UDCA | 5 | 9,12 | 10 | 5,02 |

Trans 3α,7β-dihydroxy-5β-24-cholen-27-oic acid (TOL-UDCA) was studied compared with ursodeoxycholic acid and the glycine and taurine conjugated thereof also in the following pharmacological tests:
hepatic and intestinal metabolism (in vivo and in vitro)
hepatic and intestinal absorption
bile secretion
effects on the secretion of bile, bile acids, cholesterol and phospholipids.

TOL-UDCA was administered to rat by intravenous and intraduodenal routes at a dose of 6 μmoles/min/kg during 1 hour.

Hepatic absorption and intestinal metabolism

When administered intravenously, TOL-UDCA is absorbed by liver and only partially secreted in bile. The compound is recovered in the bile with a slow kinetic and it is poorly conjugated with glycine and taurine. On the contrary, UDCA is completely transformed into the conjugated forms thereof, i.e. tauro-UDCA and, to a lesser extent, glyco-UDCA.

At the end of the infusion, TOL-UDCA disappears from the bile with a slow kinetic and a noticeable amount of this bile acid is still present 2 hours after.

When administered intraduodenally, TOL-UDCA is efficiently absorbed by intestine with a higher recovery than that of glyco-UDCA and tauro-UDCA.

When incubated with human faeces under aerobic and anaerobic conditions, the compound is poorly metabolized (7-dehydroxylate) with a significantly lower kinetic than that of UDCA and of the conjugated forms thereof.

Effect on bile flow and bile lipid secretion

Intravenous administration of TOL-UDCA increases bile flow and this effect is stronger than the one of UDCA natural analogs and of the conjugated forms thereof (see Table 2).

TABLE 2

| Effect of TOL-UDCA on bile flow and secretion | | | |
|---|---|---|---|
| | $SM_{V_0}$ μl/min/kg | $SM_{AB}$ | $SM_{XOL}$ μmol/min/kg | $SM_{PL}$ |
| UDCA | 60 | 3,02 | 0,022 | 0,22 |
| T-UDCA | 35 | 2,40 | 0,014 | 0,18 |
| G-UDCA | 40 | 2,10 | 0,028 | 0,39 |
| TOL-UDCA | 90 | 1,02 | 0,020 | 0,12 |

$SM_{V_0}$ = maximum bile flow
SM = maximum bile lipid secretion

No significant differences are evidenced on cholesterol and phospholipid transport and secretion compared with UDCA and its conjugated forms.

The pharmacokinetic characteristics of compound TOL-UDCA can be summarized as follows:

a) efficient absorption by liver and poor secretion in bile, as a consequence of a poor conjugation;

b) very good absorption by intestine after intraduodenal administration, to a higher degree than natural analogs such as glyco-UDCA and tauro-UDCA, as a consequence of both the active and passive transports;

c) very slow intestinal metabolization, particularly 7-dehydroxylation, compared with UDCA, likely as a consequence of a good resistance to intestinal bacterial flora;

d) strong choleretic effect after intravenous or intraduodenal administrations, which effect is higher than that of UDCA.

In conclusion, the compounds of the invention provide an improvement in the structure/activity studies, since the presence of a double bond in the side chain give the compounds an optimum conformation for intestinal absorption. Hepatic absorption is also efficient.

Therefore a compound such as TOL-UDCA, which accumulates in the hepatic cells, can advantageously be used in the treatment of cholestatic syndromes.

We claim:

1. Compounds of formula I

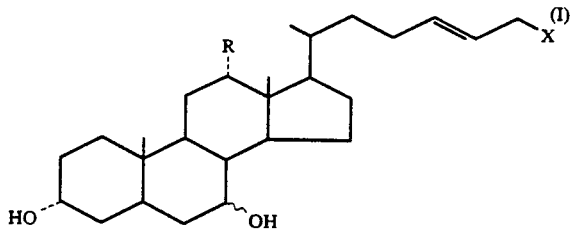

wherein:
R is hydrogen or hydroxy;
X is a carboxy or a $SO_3H$ group.

2. Compounds of formula I wherein X is a carboxy group.

3. Compounds of claim 1, wherein R is hydroxy and the hydroxy group in 7 is in α configuration.

4. Compounds of claim 1, wherein R is hydrogen and the hydroxy group in 7 is in α configuration.

5. Compounds of claim 1, wherein R is hydrogen and the hydroxy group in 7 is in β configuration.

6. Compounds of claim 1, wherein R is hydroxy and the hydroxy group in 7 is in β configuration.

7. A pharmaceutical composition having choleretic, anticholestatic and antilithiasis activities which comprises as the principal active ingredient an effective amount of a compound according to claim 1 in admixture with a pharmaceutically acceptable carrier.

8. A method of treating cholestatic syndromes which comprises administering to a patient an effective amount of a compound according to claim 7.

* * * * *